United States Patent [19]

Eisner et al.

[11] Patent Number: 4,728,290
[45] Date of Patent: Mar. 1, 1988

[54] DENTAL HAND PIECE SHIELD OR PROPHYLACTIC

[76] Inventors: Mark R. Eisner, 3130 Turner St., Allentown, Pa. 18104; James M. Hatfield, Jr., 45 Linden Pl., Summit, N.J. 07901

[21] Appl. No.: 43,497

[22] Filed: Apr. 28, 1987

[51] Int. Cl.⁴ .................................................. A61C 1/16
[52] U.S. Cl. ...................................................... 433/116
[58] Field of Search ......................................... 433/116

[56] References Cited

U.S. PATENT DOCUMENTS

| | | |
|---|---|---|
| 949,273 | 2/1910 | Hinrichsen . |
| 1,162,941 | 12/1915 | Martin et al. . |
| 1,342,968 | 6/1920 | Moolten . |
| 1,470,162 | 10/1923 | Gruss . |
| 1,485,963 | 3/1924 | Curry . |
| 1,691,823 | 11/1928 | Ogilvie . |
| 1,742,061 | 12/1929 | Curry . |
| 1,834,726 | 12/1931 | Ozon . |
| 2,041,077 | 5/1936 | Lininger . |
| 2,073,137 | 3/1937 | Bimrose ............................. 433/116 |
| 4,266,935 | 5/1981 | Hoppe ................................ 433/116 |
| 4,286,950 | 9/1981 | Hawk . |

Primary Examiner—Robert Peshock
Attorney, Agent, or Firm—Sanford J. Piltch

[57] ABSTRACT

A dental hand piece protective covering, shield or prophylactic comprised of a thin, tear-resistant, semi-rigid but elastic material which is sterile and disposable for covering the entirety of each of several different types of dental hand pieces providing opposing top and bottom apertures therein for access to the releasable securing means for the dental bur or other dental tool, clearance for operation of the bur or other dental tool and an air exhaust port for the air-driven turbines. The apparatus will significantly reduce and/or prevent the spread of disease through the re-use of non-sterile dental hand pieces.

34 Claims, 13 Drawing Figures

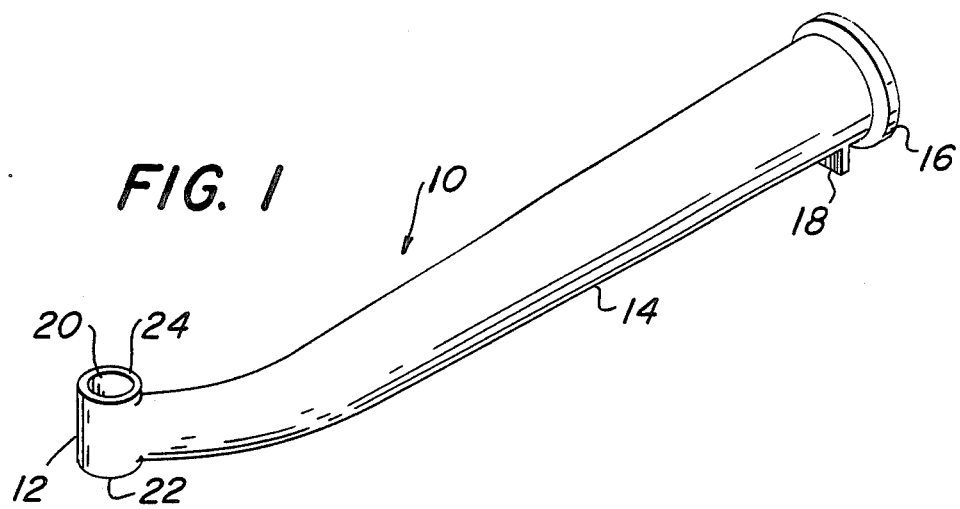
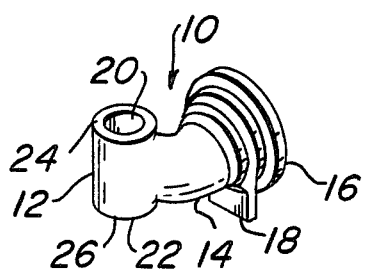
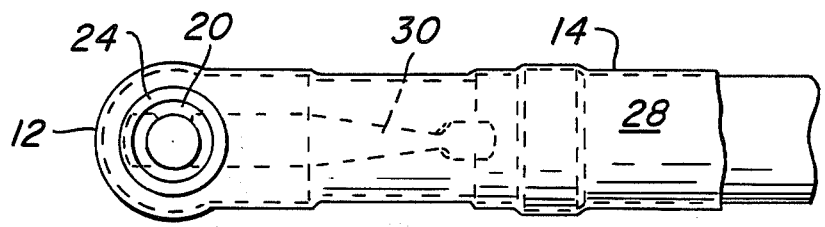
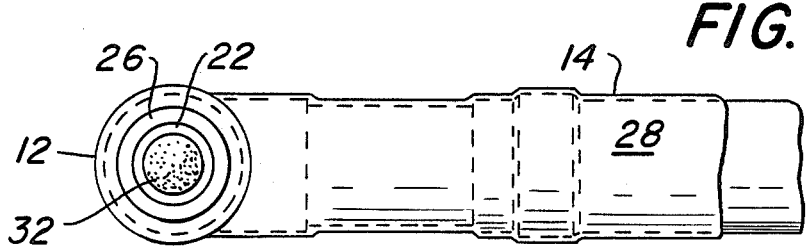

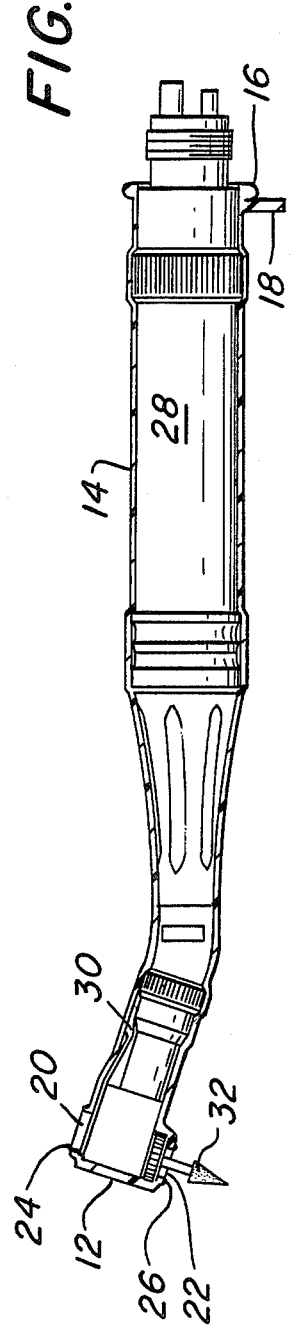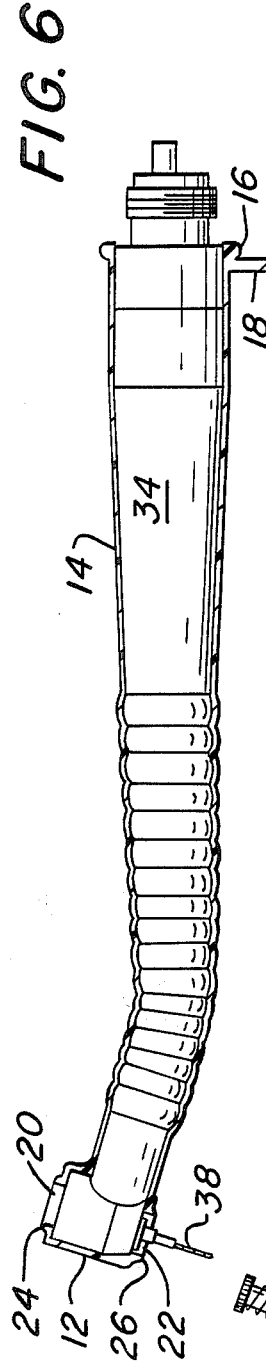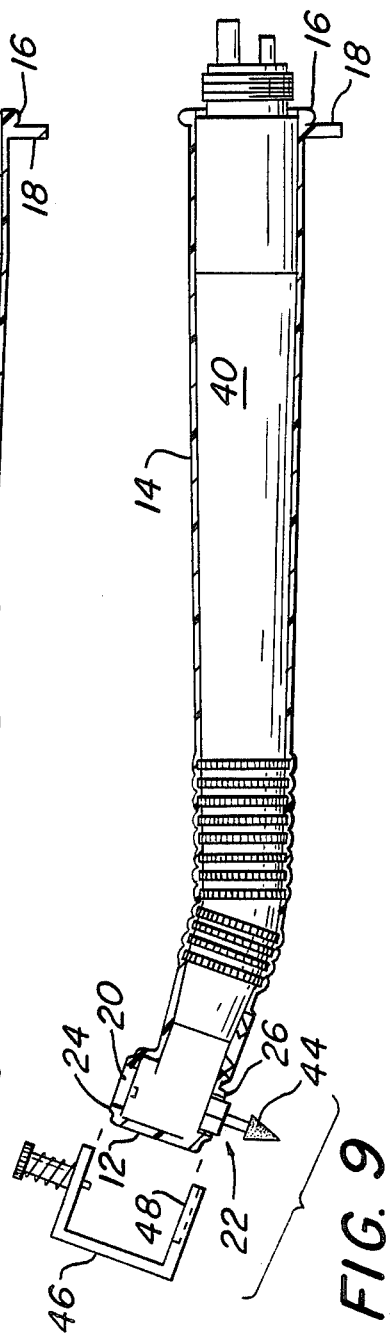

DENTAL HAND PIECE SHIELD OR PROPHYLACTIC

BACKGROUND OF THE INVENTION

Dental practitioners have been aware for years that the repeated insertion of the dental hand piece into the mouths of several different patients without sterilization of the hand piece between such uses can bring about the spread of contagious diseases. Such contagious or communicable diseases are borne in or on the body fluids and/or tissues which become attached to the exterior surfaces of the hand piece. More recently the spread of the Hepatitis virus and the Acquired Immune Deficiency virus have caused great concern for dental practitioners, not only for their patients, but also for their own health and well-being.

Both the Hepatitis virus and the Acquired Immune Deficiency virus are carried in or on body fluids and/or tissues. In the environment in which dental practitioners work, i.e. inside the mouth, body fluids such as saliva, blood, etc. and the tissues comprising the gum and portions of the teeth, the pulp and root, may potentially transmit the virus through contact. The process of cleaning and/or repairing teeth by filling caries or performing a root canal procedure requires the drilling of the teeth and the subsequent scattering of tissue particles and body fluids about the mouth. Some of those particles and/or fluids become attached to adhere to the dental hand piece. Cleaning and sterilizing the hand piece between patients has been a serious problem for dental practitioners because of its construction.

The straight pulley driven dental hand piece was attached to the drive unit by a series of pulleys comprising several gears and belts. It was extremely difficult to remove the hand piece for sterilization even at the conclusion of the day's work. Dental practitioners were reduced to wiping the hand piece with solutions to disinfect the exterior and any inner surfaces which were reachable. These procedures were not extremely effective. If the hand piece were removed, it could be placed in an auto-clave unit for sterilization by subjecting it to extremely high temperatures. However, upon remounting, the hand piece required lubrication or its functioning over the wide range of speeds would be severely hampered if not totally impaired. Most dental practitioners relied on the disinfectant solutions rather than chance the loss of the rather expensive hand piece by attempting removal, cleaning, remounting and lubrication.

Even the newer dental hand pieces capable of extremely high speeds are difficult to clean and sterilize. In addition to the problem of removal and reattachment, the relatively small sized dental hand pieces have angled-heads containing high speed air-driven turbines for providing the motive force for the various dental tools. The air-driven turbines are extemely sensitive to the corroding effects of an auto-clave unit; high temperatures, chemical agents and the resulting moisture during cooling. Lubrication of the miniature mechanisms may not be sufficient to return the high speed air-driven turbine to its fully operational capabilities.

Early attempts at creating protective coverings for the dental hand piece were relatively unsuccessful. Some examples of protective coverings to provide better sanitary conditions in the dental practitioner's office are the devices disclosed in U.S. Pat. Nos. 949,273 (Hinrichsen), 1,162,941 (Martin, et al.), 1,342,968 (Moolten), 1,470,162 (Gruss), 1,691,823 (Ogilvie), 1,742,061 (Curry) and 2,041,077 (Lininger). The Hinrichsen, Gruss and Lininger patents disclose protective coverings made of rigid materials, such as metals, of either one or two piece construction, which can be placed over the hand piece and removed for cleaning. The Martin, et al., Moolten, Ogilvie and Curry patents disclose attempts to incorporate flexible materials and/or thinner and lighter materials into the coverings to alleviate the problems of lack of manipulative control over the hand piece with the cover in place and the lack of tight fitting joints which permitted the fluids and tissue materials to get under the protective coverings.

Later attempts to improve and overcome the limitations of earlier versions of protective coverings brought into wider use elastic materials. Some examples of protective coverings using and/or incorporating elastic-type materials are disclosed in U.S. Pat. Nos. 1,485,963 (Curry), and 2,073,137 (Bimrose). These devices partially eliminated the problem of tight fitting joints and remedied, to a limited extent, the problem of manipulative control.

However, a new problem arose with the use of the tight fitting elastic materials. Ease of installation and removal was lacking as was the ability to change a bur or other dental tool without removal of the covering entirely. Further the elastic material most commonly used was natural rubber which, when wet, became slippery and difficult to hold. Although these elastic protective coverings may have solved some of the problems encountered by dental practitioners with the rigid coverings, they were not widely accepted and are not believed to be in use today.

Compared to the foregoing attempts at solving the problems of providing a workable protective covering a more recent attempt appears to be nothing more than using newer materials in the old way. U.S. Pat. No. 4,266,935 (Hoppe) discloses a protective sleeve of elastic material for pulling over the hand piece. The single piece construction appears to provide for the variety of angled hand pieces in use today but does not take into account the motive force for driving the drill or other dental tool. Modern dental hand pieces are driven by using compressed air forced through a miniature turbine. The turbine is attached to a chuck which is adaptable for holding a variety of dental tools of varying shaft length and diameter. The air, once used to power the turbine, requires an exhaust port. Without provision for the release of air through an exhaust the turbine will stop resulting in the loss of motive force to the dental tool.

This recent development of using a single piece construction to alleviate earlier problems in protective coverings gives rise to additional problems. The lack of an air exhaust port makes this device usable only on earlier models of the dental hand piece which still use a pulley drive. There still exists the problem of removing the protective sheath entirely to change a bur or other dental tool. It is also questionable whether a pre-formed sheath as disclosed in Hoppe will be capable of being installed on the hand piece with the bur or other dental tool in place without ripping or tearing, or damaging the dental tool.

In recent years dental practitioners have become increasingly aware of the rapid spread of communicable diseases through body fluids and tissues such as may be dislodged and/or become attached to the dental hand piece during its use in the mouth of a patient. In fact, dental practitioners have been cautioned to protect themselves from infection by using sterile gloves and masks and to use protective glasses when practicing dentistry on their patients. Very recently the rapid spread of the Hepatitus virus and the Acquired Immune Deficiency virus has caused significant concern among dental practitioners. The American Dental Association and other professional organizations have strongly urged that dental practitioners take additional steps to decrease the chance of spreading the disease through the use of non-sterile implements.

It is therefore an object of the present invention to provide a sterile protective covering or shield for the dental hand piece to significantly reduce o prevent the spread of contagious, communicable diseases.

It is a further object of the present invention to provide such a shield which is disposable after a single use and which is easily applied and removed so that it will have wide-spread acceptance in the dental professions.

It is another object of the present invention to provide such a shield which is highly elastic and stretchable, yet tear resistant, and which is capable of covering the entirety of a variety of dental hand pieces.

It is also an object of the present invention to provide such a shield with allows access to the releasable securing mechanism of each hand piece so that a dental practitioner or other dental professional need not remove the shield in order to change or adjust the dental tool.

It is also an object of the present invention to provide a shield which can accomodate the newer air-driven hand pieces which require an air exhaust port and to provide for hand piece incorporated lights and water spray attachments.

Other objects will appear hereinafter.

SUMMARY OF THE INVENTION

The dental hand piece protective covering, shield or prophylactic of the present invention is comprised of a thin, tear-resistant, semi-rigid but elastic material which is sterile and disposable for covering the entirety of each of several different types of dental hand pieces. The shield has opposing top and bottom apertures for providing access to the releasable securing means for the bur or other dental tool and sufficient clearance for operation of the bur or other dental tool. The top aperture also provides an air exhaust port for the air-driven turbines.

The present invention is an apparatus for significantly reducing or preventing the spread of communicable diseases which may be transmitted by or through contact with human body fluids and tissues during dental procedures. The apparatus comprises a removable, disposable, sterile dental hand piece shield or prophylactic for placemant over and in proximate contact with a dental hand piece, having head, arm, and handle portions. The shield is used to significantly reduce the spread of communicable diseases during a first and subsequent uses of the dental hand piece in conjunction with the treatment of two or more patients eliminating the need for repeated sterilization of said dental hand piece between such uses for two or more patients.

The shield or prophylactic is comprised of a head portion and a skirt or sleeve portion. The head portion is substantially cylindrical and has opposing substantially annular apertures in the top and bottom thereof. The head portion also has an extension protruding outward from the side for connecting to and mating with the skirt or sleeve portion. The bottom aperture of the head portion provides an opening with clearance sufficient for attachment, detachment and operation of a dental bur or other similar tool without contacting the rim of the opening. The top aperture provides an opening with clearance sufficient for manipulation of the dental bur or other similar tool releasable securing mechanism or means and for exhaust of the air from the dental bur or other similar tool drive means. The skirt or sleeve portion is substantially annular over its entire length along the arm and handle portions of the dental hand piece and has an extension at its proximal end over the arm portion of the dental hand piece for connecting to and mating with the extension of the head portion. The skirt or sleeve portion also has a reinforcing collar at its distal end. Attached to the collar is a tab which may be used to ease the application and removal of the shield. Additionally, medicaments may be applied to the internal surface of the shield to continue disinfection and to provide a means of lubricating the shield for ease in application and removal.

The shield or prophylactic of the present invention may also be configured to permit the encompassing of a water spraying means and an illuminating means within the bottom aperture or in a second bottom aperture.

BRIEF DESCRIPTION OF THE DRAWINGS

For the purpose of illustrating the invention, there are shown in the drawings forms which are presently preferred; it being understood, however, that the invention is not limited to the precise arrangement and instrumentalities shown.

FIG. 1 is an isometric view of the dental hand piece shield or prophylactic of the present invention.

FIG. 2 is an isometric view of the dental hand piece shield or prophylactic of the present invention in collapsed form.

FIG. 3 is a partly broken away view of a dental hand piece with the dental hand piece shield or prophylactic of the present invention installed thereon.

FIG. 4 is a top view of the head portion of the partly broken away view of a dental hand piece with the dental hand piece shield or prophylactic of the present invention installed thereon as shown in FIG. 3.

FIG. 5 is a bottom view of the head portion of the partly broken away view of a dental hand piece with the dental hand piece shield or prophylactic of the present invention installed thereon as shown in FIG. 3.

FIG. 6 is a partly broken away view of another type dental hand piece with the dental hand piece shield or prophylactic of the present invention installed thereon.

FIG. 9 is a partly broken away view of another type dental hand piece with another embodiment of the dental hand piece shield or prophylactic of the present invention installed thereon.

DETAILED DESCRIPTION OF THE INVENTION

Figure 7:
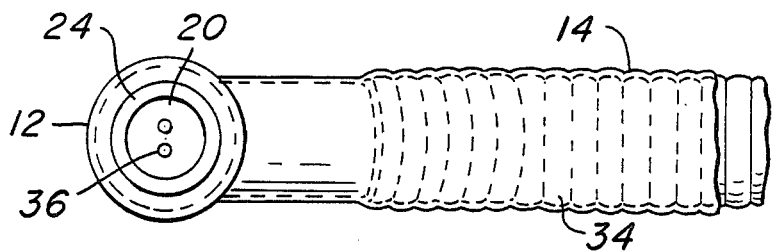
FIG. 7 is a top view of the head portion of the partly broken away view of another type dental hand piece with the dental hand piece shield or prophylactic of the present invention installed thereon as shown in FIG. 6.

The following detailed description is of the best presently contemplated modes of carrying out the present invention. This description is not intended in a limiting sense, but is made solely for the purpose of illustrating the general principles of the invention.

Referring now to the drawings in detail, wherein like numerals represent like elements, there is shown in FIG. 1 a dental hand piece shield or prophylactic 10. The shield or prophylactic 10 has two portions, the head 12 and the skirt or sleeve 14. The head portion is substantially cylindrical in shape in order to accomodate the various different types of dental hand piece heads. The skirt or sleeve 14 is substantially annular in shape in order to snugly fit over the arm and handle portions of the various dental hand pieces. Located at the distal end of the skirt or sleeve 14 is a collar 16. Attached to the underside of the collar 16 is tab 18 used in the application and/or removal of the shield or prophylactic 10. FIG. 2 shows the shield or prophylactic 10 in a collapsed state. All of the foregoing elements will be described more fully hereinafter.

The shield or prophylactic 10 is comprised of an elastomer of differing thicknesses and having the following properties. The elastomer may be of any natural or man-made materials, or combinations thereof, including rubber, latexes, polymers, and/or any other natural or man-made material. The elastomer must exhibit a sufficient coefficient of elasticity so as to return to its original shape and size or as nearly thereto as practicable. The elastomer must also be sufficiently elastically deformable to be pulled over the head of a dental hand piece. The elastomer must also exhibit sufficient toughness and tear-resistantance to withstand the forces applied to it from pulling and/or stretching during application and/or removal. Finally, the elastomer must provide a medium to high degree of friction contact on the exterior surface of at least the skirt or sleeve portion to insure complete manipulative control of the dental hand piece with the shield or prophylactic 10 in place.

The thickness of the elastomer at any given point along the shield or prophylactic 10 is directly dependent upon the required function at that point. For example the skirt or sleeve 14 will range between 0.5 and 5 mils thickness along almost its entire length. The skirt or sleeve 14 is preferred to be in the range of 3-5 mils thickness. However, the collar 16 and tab 18 which are required to be thicker elements due to their respective functions in the application and/or removal process. The collar 16 and tab 18 are preferred to be in the range of 3-15 mils thickness but may range as high as 30 mils thickness. The nominal relaxed diameter of the skirt or sleeve 14 is preferred to be in the range of 0.25 inches to 0.375 inches.

The head portion of the shield or prophylactic 10 is of thicker construction than the skirt or sleeve 14. The head 12 is also preferred to be in the range of 3-15 mils thickness but may range as high as 30 mils thickness. The head 12 is configured substantially in a cylindrical shape but is also made of an elastomer material and, as such, is deformable within the limits of its thickness. The head 12 has opposing apertures on its top and bottom, 20 and 22, respectively. The top aperture 20 has a rim 24 of thicker elastomer material creating a semi-rigid edging around the opening in the top of the head 12. The semi-rigid opening or top aperture 20 provides access to and manipulation of the releasable securing meachanism or means for attaching and detaching a dental bur or other dental tool from the dental hand piece.

The top aperture 20 also provides an air exhaust port for the air-driven miniature turbine housed within the head of the dental hand piece. The exhaust port is necessary for without the port the air-driven turbine would stop from the back pressure created. The top aperture 20 need only be as large as is necessary to accomodate the insertion of the tool for releasing or securing the dental bur or other dental tool into the releasable securing mechanism and for the air exhaust port. The air exhaust port is normally spaced outward of and surrounds the releasable securing mechanism. The aperture 20 should be kept as small as possible to protect the integrity of the shield 10.

The bottom aperture 22 has a rim 26 of thicker elastomer material creating a semi-rigid edging around the opening in the bottom of the head 12. The semi-rigid opening or bottom aperture 22 provides sufficient clearance for the insertion of a dental bur or other dental tool into a chuck or other the releasable securing means and for the normal range of operations of the dental bur or other dental tool without impingement on that operation due to contact with the shield or prophylactic 10. The bottom aperture 22, similarly to the top aperture 20, should be kept small so as to accomodate only the insertion, removal and operation of the dental bur or other dental tool in order to preserve the integrity of the shield 10.

Due to its elastic properties the shield or prophylactic 10 may be collapsed into substantially the form shown in FIG. 2. In this form the shield or prophylactic 10 will suffer less chance of damage from the completion of manufacture until application and use. The collapsed or accordianized form of the shield or prophylactic 10 will make for greater ease in application as the shield will not have to be compressed, collapsed or accordianized by the dental practitioner which action may damage the shield.

Referring now to FIGS. 3, 4 and 5, there is shown in FIG. 3 a dental hand piece having a latch-type releasable securing means for the dental bur or other dental tool. This latch-type dental hand piece 28 has head, arm and handle portions. The shield or prophylactic 10 is shown as it would be applied to the hand piece 28 by reference numerals 12, 14. The shield or prophylactic 10 adapts to the varying thicknesses, depressions, appendages and other exterior surface shapes and irregularities of the dental hand piece 28 and fits snugly thereon because of its elastic properties. The latch 30, shown in partial phantom in FIG. 4, is easily manipulable within the shield or prophylactic 10 without removal thereof. The latch handle need only be pivoted about its midpoint approximately 30 degrees from its closed position to allow for the attachment, adjustment or removal of the dental bur or other dental tool 32. This action will temporarily distort but will not tear the shield 10. For this type of hand piece the dental bur or other dental tool 32 has a long shank or shaft with an indenture at the top for engaging with the latch 30. Thus, the dental bur or other dental tool 32 may be inserted, removed to be changed for another, or adjusted while the shield or prophylactic 10 remains in place. The top aperture 20 provides a means to view the movement of the latch 30 as it engages with or disengages from the shaft of the dental tool and for the air exhaust port required for operation of an air-driven hand piece. The bottom aperture 22 provides the necessary clearance for normal operation of the dental bur or other dental tool 32 and access for insertion into the turbine and latch mechanism.

Figure 8:
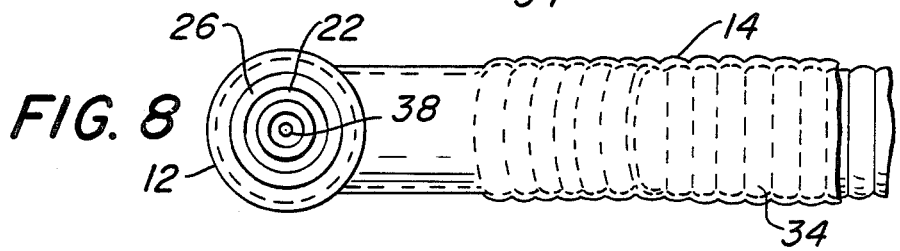
FIG. 8 is a bottom view of the head portion of the partly broken away view of another type dental hand piece with the dental hand piece shield or prophylactic of the present invention installed thereon as shown in FIG. 6.
Figure 10:
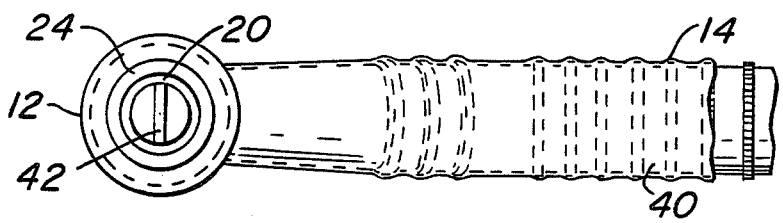
FIG. 10 is a top view of the head portion of the partly broken away view of another type dental hand piece with another embodiment of the dental hand piece shield or prophylactic of the present invention installed thereon as shown in FIG. 9.

Referring now to FIGS. 6, 7 and 8, there is shown in FIG. 6 another dental hand piece having a chuck-type releasable securing means for the dental bur or other dental tool. The chuck-type dental hand piece 34 has head, arm and handle portions similarly to the latch-type hand piece 28. The shield or prophylactic 10 is shown as it would be applied to the hand piece 34 by reference numerals 12, 14. The shield or prophylactic 10 adapts to the varying thicknesses, depressions, appendages and other exterior surface shapes and irregularities of the dental hand piece 34 and fits snugly thereon because of its elastic properties. The top aperture 20 gives access to the tightening and release mechanism 36 of the releasable securing means so that the dental bur (or other dental tool) 38 may be inserted, removed or changed for another, or adjusted while the shield or prophylactic 10 remains in place. The bottom aperture 22 provides the necessary clearance for normal operation of the dental bur (or other dental tool) 38 and access for insertion into the chuck.

Referring now to FIGS. 9 through 13, there is shown in FIG. 9 another dental hand piece having a chuck-type releasable securing means for the dental bur or other dental tool with a water spraying means and an illuminating means. The chuck-type dental hand piece with the water spraying means and/or the illuminating means 40 has head, arm and handle portions similarly to the other two hand pieces 28, 34. The shield or prophylactic is shown as it would be applied to the hand piece 40 by reference numerals 12, 14. The shield or prophylactic adapts to the varying thicknesses, contours, depressions, appendages, and other exterior surface shapes and irregularities of the dental hand piece and fits snugly thereon because of its elastic properties. The top aperture 20 gives access to the tightening and release mechanism 42 of the releasable securing means so that the dental bur or other dental tool 44 may be inserted, removed or changed for another, or adjusted while the shield or prophylactic 10 remains in place. The bottom aperture 22 provides the necessary clearance for normal operation of the dental bur or other dental tool 44 and access for insertion into the chuck.

The releasable securing means for the hand piece 40 has a separate dental tool carrier and tightening and release mechanism tool 46. The C-shaped carrier/tool 46 fits over the head of the hand piece 40 while carrying the dental bur or other dental tool 44 in its tray 48. The control knob 50 is mounted on a spring 52 which keeps the knob 50 elevated and out of contact with the tightening and release mechanism 42. When inserting or adjusting the dental bur or other dental tool 44 the C-shaped tool 46 is placed over the head of the hand piece 40, the dental bur 44 pushed upward into the chuck in the hand piece, and the knob 50 pressed down into contact with the tightening and release mechanism 42 and turned to lock the dental bur 44 in place for use. When removing the dental bur 44 the process is reversed. For adjustment, a combination of the insertion and removal procedures is used.

Figure 11:
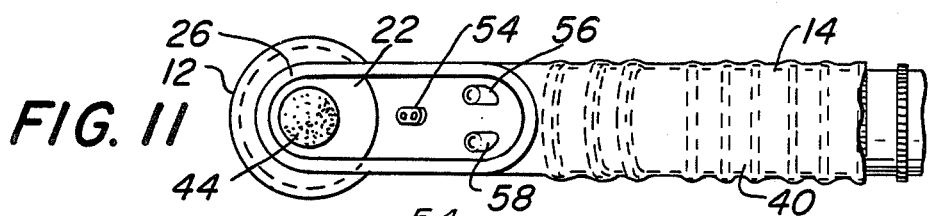
FIG. 11 is a bottom view of the head portion of the partly broken away view of another type dental hand piece with another embodiment of the dental hand piece shield or prophylactic of the present invention installed thereon as shown in FIG. 9 with an elongated bottom aperture for accomodating a water spray and illuminating means.
Figure 12:
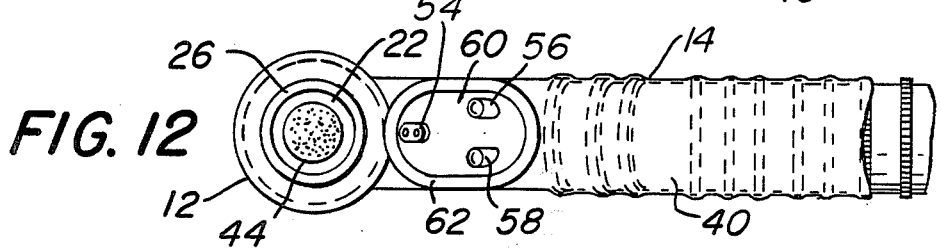
FIG. 12 is a bottom view of the head portion of the partly broken away view of another type dental hand piece with another embodiment of the dental hand piece shield or prophylactic of the present invention installed thereon as shown in FIG. 9 with another embodiment of the bottom aperture showing two bottom apertures for accomodating a water spray and illuminating means.
Figure 13:
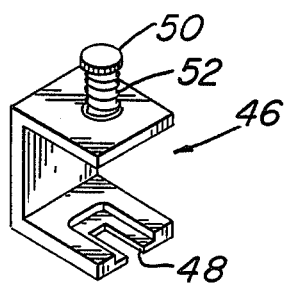
FIG. 13 is an isometric view of a dental tool mounting means for attaching and detaching a dental bur or other similar tool for use with the embodiment shown in FIG. 9.

The hand piece 40 also includes a water spraying means 54 for cooling the dental bur or other dental tool 44 and/or the tooth when drilling, filing or polishing. The water spraying means is shown in FIGS. 11, 12 as a nozzle angled downward toward the extended tip of the dental bur or other dental tool 44. As the dental tool 44 is operated a steady spray of water emanates from the nozzle 54. An illuminating means may also be included in the hand piece 40. The illuminating means shown as the ends of two focused fiber optic strands 56, 58 provide light to a designated area approximately located at the farthest extension of the dental tool 44. The fiber optic strands 56, 58 are provided at their other ends with a light source of sufficient strength to illuminate the desired area under study by the dental practitioner. In order to provide for the water spraying means 54 and the illuminating means 56 and 58, the bottom aperture 22 must be altered to preserve the integrity of the shield or prophylactic 10 and limit the amount of hand piece surface area which is exposed.

The bottom aperture 22 can, in a first embodiment shown in FIG. 11, be elongated to include the water spraying means 54 and the illuminating means 56, 58 within the opening. An alternate embodiment is shown in FIG. 12 where a second bottom aperture 60 with a rim 62 of thicker elastomer material creating a semi-rigid edging around the second bottom opening for the water spraying means 54 and the illuminating means 56, 58. This second bottom aperture 60 is similar to the bottom aperture 22 and may take an annular, circular, or elongated shape depending upon the location and placement of the water spraying means 54 and the illuminating means 56, 58.

A problem can arise during application of the shield or prophylactic, i.e. orientation. The orientation problem can be alleviated by color-coding the top and bottom apertures in the head portion 12 of the shield 10, striping the skirt or sleeve portion 14 of the shield 10 on its top, making the sizes of the top and bottom apertures 20, 22 differently sized, placing the tab 18 in a particular location, i.e. top, side, or any other suitable means to accomplish the purpose.

It is also possible to aid in the sterilization process by placing aseptic medicaments on the inner surface of the shield 10 for additional disinfecting. This will ease the application of the shield by providing a lubricating means between the exterior surface of the hand piece and the inner surface of the shield or prophylactic 10.

The head 12 and skirt or sleeve 14 of the shield or prophylactic 10 may be manufactured from the same or different elastomeric materials. It is presently contemplated to manufacture the head 12 by an injection molding process known to those skilled in the art to create a semi-rigid, but elastic, head portion 12. The molded head 12 will have an annular extension protruding outward from its side for connecting to and mating with the skirt or sleeve 14. The skirt or sleeve 14 will be formed directly on the extension of the head 12 creating a heat-sealed joint during the formation process. An analogous process would be that for forming the screw head of a toothpaste tube and joining the multi-layed laminate of the tube portion thereto. Thus, an elastic skirt or sleeve 14 will be joined to the injection molded semi-rigid head 12 to form the shield or prophylactic 10 of the present invention.

An alternative method of manufacture is to provide the shield or prophylactic 10 made of heat shrinkable material with die cut apertures for access to the dental bur or other tool and to the releasable securing means. The heating application can be made at the site of application by means of a heat lamp or other means. The heat shrinkable material is preferred to be a single rolled sleeve of 0.5 mils thickness. In the case of the heat shrinkable material a transparent or substantially translucent material can be used to decrease the size of the bottom aperture 22 if the hand piece includes illuminating means 56, 58.

The shield or prophylactic 10 is used in the following manner. The hand piece should first be sterilized using an ethylene oxide or other suitable gas or heat in an auto-clave unit. A sterile packaged disposable shield or prophylactic 10 should be applied to the hand piece with sterile gloves by placing the head 12 of the shield over the head portion of the hand piece and rolling or stretchably extending the skirt or sleeve 14 over the arm and handle of the hand piece pulling on the tab 18 at the collar 16 to confirm a snug fit over the entire length of the hand piece. A sterilized dental bur or other dental tool may then be inserted into the hand piece. The hand piece is ready for use with a patient.

During use with a single patient, the dental bur or other dental tool may be tightened, adjusted, or exchanged for another without removing the shield or prophylactic 10. After completing the treatment of the patient the shield can be removed by first removing the dental bur or other dental tool and then by pulling on the tab 18 so that the shield or prophylactic 10 is peeled off by turning itself inside out. This procedure retains the droplet of liquid and attached tissue inside the reversed shield or prophylactic 10. Thus, the potentially communicable virus borne on the human body liquids and tissues can be safely disposed by sealing the shield in an impervious container for destruction in an appropriate manner. Once the shield or prophylactic 10 is entirely removed from the hand piece the minimal surface areas of the hand piece not having been covered by the shield may be disinfected using an appropriate disinfectant solution. The cloth used to wipe the potentially affected areas should be disposed of in the impervious container with the shield. The process may now be repeated for the next patient.

The shield or prophylactic 10 of the present invention can be used with all types of dental hand pieces due to its ability to adapt and/or conform to the variety of exterior shapes of the various hand pieces. The dental hand pieces with which the present invention may be used include, but are not limited to, cavitron, low and high speed, reduction angle, contra-angle, and pulp testing hand pieces.

The present invention provides a significant step forward in reducing the rapid spread of contagious, communicable diseases of the Hepatitus and Acquired Immune Deficiency viral type which are borne on the body fluids and tissues of humans. The shield or prophylactic 10 provides a substantially sterile surface on the exterior of a dental hand piece which, without the shield, would be a likely place for the transmittance of the diseases.

The present invention may be embodied in other specific forms without departing from the spirit or essential attributes thereof and, accordingly, reference should be made to the appended claims, rather than to the foregoing specification, as indicating the scope of the invention.

We claim:

1. A removable disposable sterile dental hand piece shield or prophylactic for placement over and in proximate contact with a dental hand piece, having head, arm, and handle portions, for significantly reducing the spread of communicable diseases which may be transmitted by or through contact with human body fluids and tissues during a first and subsequent uses of the dental hand piece in conjunction with the treatment of two or more patients eliminating the need for repeated sterilization of said dental hand piece between such uses for the two or more patients comprising a head portion and a skirt or sleeve portion; said head portion being substantially cylindrical, having opposed substantially annular apertures in the top and bottom thereof and having an extension protruding outward from the side of the head portion for connecting to and mating with the skirt or sleeve portion, said bottom aperture providing an opening with clearance sufficient for attachment, detachment and operation of a dental bur or other tool without contacting the rim of the opening, said top aperture providing an opening with clearance sufficient for manipulation of the dental bur or other tool releasable securing means and for exhaust of the air from the dental bur or other tool turbine drive means; said skirt or sleeve portion being substantially annular over its entire length along the arm and handle portions of the dental hand piece, having an extension at its proximal end over the arm portion of the dental hand piece for connecting to and mating with the extension of the head portion and having at its distal end a reinforcing collar.

2. In accordance with claim 1 wherein said head portion has a thickness in the range between 3 and 30 mils.

3. In accordance with claim 1 wherein said skirt or sleeve portion has a thickness in the range between 0.5 and 5 mils.

4. In accordance with claim 1 wherein said skirt or sleeve portion has a nominal diameter in its relaxed state in the range between 0.25 and 0.375 inches.

5. In accordance with claim 1 wherein said reinforcing collar of the skirt or sleeve portion has a thickness in the range between 3 and 30 mils for maintaining the shield in its fully distended position.

6. In accordance with claim 1 wherein said reinforcing collar of the skirt or sleeve portion has a tab distending therefrom for use in applying and/or removing the shield, said tab having a thickness in the range between 3 and 30 mils.

7. In accordance with claim 1 wherein said top aperture has a rim providing a semi-rigid opening for maintaining the sterile integrity of the shield about the opening, said rim having a thickness in the range between 3 and 30 mils.

8. In accordance with claim 1 wherein said bottom aperture has a rim providing a semi-rigid opening for maintaining the sterile integrity of the shield about the opening, said rim having a thickness in the range between 3 and 30 mils.

9. In accordance with claim 1 wherein said bottom aperture is elongated to encompass a water spraying means located in the proximal portion of the arm of the hand piece.

10. In accordance with claim 1 wherein said bottom aperture is elongated to encompass an illuminating means located in the proximal portion of the arm of the hand piece.

11. In accordance with claim 1 wherein said bottom aperture is elongated to encompass a water spraying means and an illuminating means located in the proximal portion of the arm of the hand piece.

12. In accordance with claim 1 wherein a second bottom aperture has a rim providing a semi-rigid opening for maintaining the sterile integrity of the shield about the opening, said rim having a thickness in the range between 3 and 30 mils provides an opening to encompass a water spraying means and an illuminating means located in the proximal portion of the arm of the hand piece.

13. In accordance with claim 1 wherein asceptic medicaments are applied to the inner surface of the head and the skirt or sleeve of the shield for continued disinfection and for lubrication in the application and removal of the shield.

14. In accordance with claim 1 wherein the outer surface of the skirt or sleeve has a medium to high degree of frictional contact.

15. In accordance with claim 1 wherein the shield is made from an elastomeric or elastic material, natural or man-made or any combination thereof.

16. In accordance with claim 15 wherein said elastomeric or elastic material exhibits sufficient deformability to stretch over the hand piece, toughness and/or tear-resistance to withstand pulling and stetching during application and/or removal and material memory to return to and/or retain its original size and shape after removal.

17. A removable disposable sterile dental hand piece shield or prophylactic for placement over and in proximate contact with a dental hand piece, having head, arm, and handle portions, for significantly reducing the spread of communicable diseases which may be transmitted by or through contact with human body fluids and tissues during a first and subsequent uses of the dental hand piece in conjunction with the treatment of two or more patients comprising a head portion and a skirt or sleeve portion; said head portion being substantially cylindrical, having opposed substantially annular apertures in the top and bottom thereof and having an extension protruding outward from the side of the head portion for connecting to and mating with the skirt or sleeve portion; said skirt or sleeve portion being substantially annular over its entire length along the arm and handle portions of the dental hand piece, having an extension at its proximal end over the arm portion of the dental hand piece for connecting to and mating with the extension of the head portion and having at its distal end a reinforcing collar.

18. In accordance with claim 17 wherein said head portion has a thickness in the range between 3 and 30 mils.

19. In accordance with claim 17 wherein said skirt or sleeve portion has a thickness in the range between 0.5 and 5 mils.

20. In accordance with claim 17 wherein said skirt or sleeve portion has a nominal diameter in its relaxed state in the range between 0.25 and 0.375 inches.

21. In accordance with claim 17 wherein said reinforcing collar of the skirt or sleeve portion has a thickness in the range between 3 and 30 mils for maintaining the shield in its fully distended position.

22. In accordance with claim 17 wherein said reinforcing collar of the skirt or sleeve portion has a tab distending therefrom for use in applying and/or removing the shield, said tab having a thickness in the range between 3 and 30 mils.

23. In accordance with claim 17 wherein said top aperture provides an opening with clearance sufficient for manipulation of the dental bur or other tool releasable securing means and for exhaust of the air from the dental bur or other tool turbine drive means.

24. In accordance with claim 17 wherein said top aperture has a rim providing a semi-rigid opening for maintaining the sterile integrity of the shield about the opening, said rim having a thickness in the range between 3 and 30 mils.

25. In accordance with claim 17 wherein said bottom aperture provides an opening with clearance sufficient for attachment, detachment and operation of a dental bur or other tool without contacting the rim of the opening.

26. In accordance with claim 17 wherein said bottom aperture has a rim providing a semi-rigid opening for maintaining the sterile integrity of the shield about the opening, said rim having a thickness in the range between 3 and 30 mils.

27. In accordance with claim 17 wherein said bottom aperture is elongated to encompass a water spraying means located in the proximal portion of the arm of the hand piece.

28. In accordance with claim 17 wherein said bottom aperture is elongated to encompass an illuminating means located in the proximal portion of the arm of the hand piece.

29. In accordance with claim 17 wherein said bottom aperture is elongated to encompass a water spraying means and an illuminating means located in the proximal portion of the arm of the hand piece.

30. In accordance with claim 17 wherein a second bottom aperture has a rim providing a semi-rigid opening for maintaining the sterile integrity of the shield about the opening, said rim having a thickness in the range between 3 and 30 mils provides an opening to encompass a water spraying means and an illuminating means located in the proximal portion of the arm of the hand piece.

31. In accordance with claim 17 wherein asceptic medicaments are applied to the inner surface of the head and the skirt or sleeve of the shield for continued disinfection and for lubrication in the application and removal of the shield.

32. In accordance with claim 17 wherein the outer surface of the skirt or sleeve has a medium to high degree of frictional contact.

33. In accordance with claim 17 wherein the shield is made from an elastomeric or elastic material, natural or man-made or any combination thereof.

34. In accordance with claim 33 wherein said elastomeric or elastic material exhibits sufficient deformability to stretch over the hand piece, toughness and/or tear-resistance to withstand pulling and stetching during application and/or removal and material memory to return to and/or retain its original size and shape after removal.

* * * * *